(12) United States Patent
Morris et al.

(10) Patent No.: US 8,804,124 B1
(45) Date of Patent: Aug. 12, 2014

(54) METHOD AND APPARATUS FOR MEASURING PROTEIN QUALITY

(71) Applicants: Craig F. Morris, Pullman, WA (US); Brian Axness, Fall City, WA (US); Brandon DeCook, Pullman, WA (US); Arthur D. Bettge, Moscow, ID (US); Stephen R. Delwiche, Baltimore, MD (US)

(72) Inventors: Craig F. Morris, Pullman, WA (US); Brian Axness, Fall City, WA (US); Brandon DeCook, Pullman, WA (US); Arthur D. Bettge, Moscow, ID (US); Stephen R. Delwiche, Baltimore, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/792,865

(22) Filed: Mar. 11, 2013

Related U.S. Application Data

(60) Provisional application No. 61/715,597, filed on Oct. 18, 2012.

(51) Int. Cl.
*G01N 21/00* (2006.01)

(52) U.S. Cl.
USPC .......................................... 356/442; 356/433

(58) Field of Classification Search
USPC ................................................... 356/432–444
See application file for complete search history.

(56) References Cited

U.S. PATENT DOCUMENTS

| | | | | |
|---|---|---|---|---|
| 4,017,192 A | * | 4/1977 | Rosenthal | 356/432 |
| 4,260,262 A | * | 4/1981 | Webster | 356/418 |
| 4,752,689 A | * | 6/1988 | Satake | 250/339.07 |
| 4,806,764 A | * | 2/1989 | Satake | 250/339.07 |
| 4,953,401 A | | 9/1990 | Perten | |
| 6,147,502 A | * | 11/2000 | Fryer et al. | 324/637 |
| 6,208,420 B1 | * | 3/2001 | Satake et al. | 356/432 |
| 6,369,388 B2 | * | 4/2002 | Rosenthal et al. | 250/343 |
| 2011/0171354 A1 | | 7/2011 | Funk et al. | |

\* cited by examiner

*Primary Examiner* — Gregory J Toatley
*Assistant Examiner* — Jarreas C Underwood
(74) *Attorney, Agent, or Firm* — Robert D. Jones; John Fado; Lesley Shaw

(57) ABSTRACT

An array of light sources (lasers) is positioned so that each of the light sources emits a beam that is directed through a sedimenting column of ground grain. Photodetectors (photodiodes) positioned opposite the light sources receive the light beams emerging from the sedimenting column and convert the beams into electronic signals. A computer processor processes the electronic signals and generates values for protein quality.

20 Claims, 6 Drawing Sheets

METHOD AND APPARATUS FOR MEASURING PROTEIN QUALITY

REFERENCE TO RELATED APPLICATIONS

This application claims the benefit of U.S. Provisional Application No. 61/715,597, filed Oct. 18, 2012, which is incorporated herein by reference in its entirety.

FIELD OF THE INVENTION

The present invention relates to a method and apparatus for measuring protein quality. Specifically, the invention relates to a method and apparatus for measuring protein quality in cereals, specifically wheat grain.

BACKGROUND OF THE INVENTION

In cereal grains (for example wheat), gluten is the functional component of protein and determines many dough and grain processing characteristics. While gluten content and protein content are predictably correlated, protein quality is not directly predictable on the basis of protein content. Protein quality (as a function of protein content) may vary dramatically based on genetic variations in wheat varieties, wheat growing conditions, variety blending, heat and insect damage, and enzymatic additions. In the grain processing art, "protein quality" is said to vary from weak to strong gluten. The characteristics of protein quality conceptually define flour quality and relate to the performance and value of wheat meals and flours.

Currently various sedimentation tests are used to measure and characterize protein quality. The two most common sedimentation tests are the Zeleny test (ICC Standard no. 116, 118; ISO 5529) (cf. Brabender Sedimat) and the SDS test (sodium doceylsulfate) (AACC International Approved Method 56-61A). (See also, Sedimentation, p. 35 in Wheat and Flour Testing Methods: A Guide to Understanding Wheat and Flour Quality: Version 2).

These existing protein characterization tests are accurate, but they are slow and require a number of hand manipulations and some ancillary equipment. They may also require milled white flour as opposed to ground whole meal or more varied types of grain. The tests are also relatively limited in the types of information they can provide, and the tests do not facilitate automated data storage and communication. The need exists for an apparatus that measures (at least) protein quality in real time. The apparatus described herein addresses this need and can also record and communicate measured data in real time and in an electronic format.

SUMMARY OF THE INVENTION

This disclosure is directed to an apparatus for determining protein quality. The apparatus includes a container configured to hold a sample of ground grain at least partially suspended in a liquid. An array of light sources is positioned along one side of the container so that the light sources are directed at the container. An array of photodetectors is positioned on the opposite side of the container from the light sources. A computer processor is in communication with the photodetectors. As a ground grain sample settles in the liquid, the light sources emit a light beam that passes through the sample and is received by the detectors. The detectors generate electronic signals which are communicated to the processor. The processor calculates a value for protein quality based on the electronic signals.

The disclosure is also directed to a method for determining protein quality. In accordance with the method, an array of light sources is positioned along one side of a container so that the light sources are directed at the container. A corresponding array of photodetectors is positioned on the opposite side of the container from the light sources. The container is then filled with a liquid and a sample of ground grain is added so that a sedimenting column of hydrated ground grain is created.

A light beam from each of the light sources is directed through the sedimenting column to a corresponding photodetector. Each of the photodetectors translates the light beam into an electronic signal. A processor receives the electronic signal generated by the photodetectors. The processor generates a value for protein quality based on the electronic signals received from the photodetectors.

DETAILED DESCRIPTION OF PREFERRED EMBODIMENTS

Figure 1:
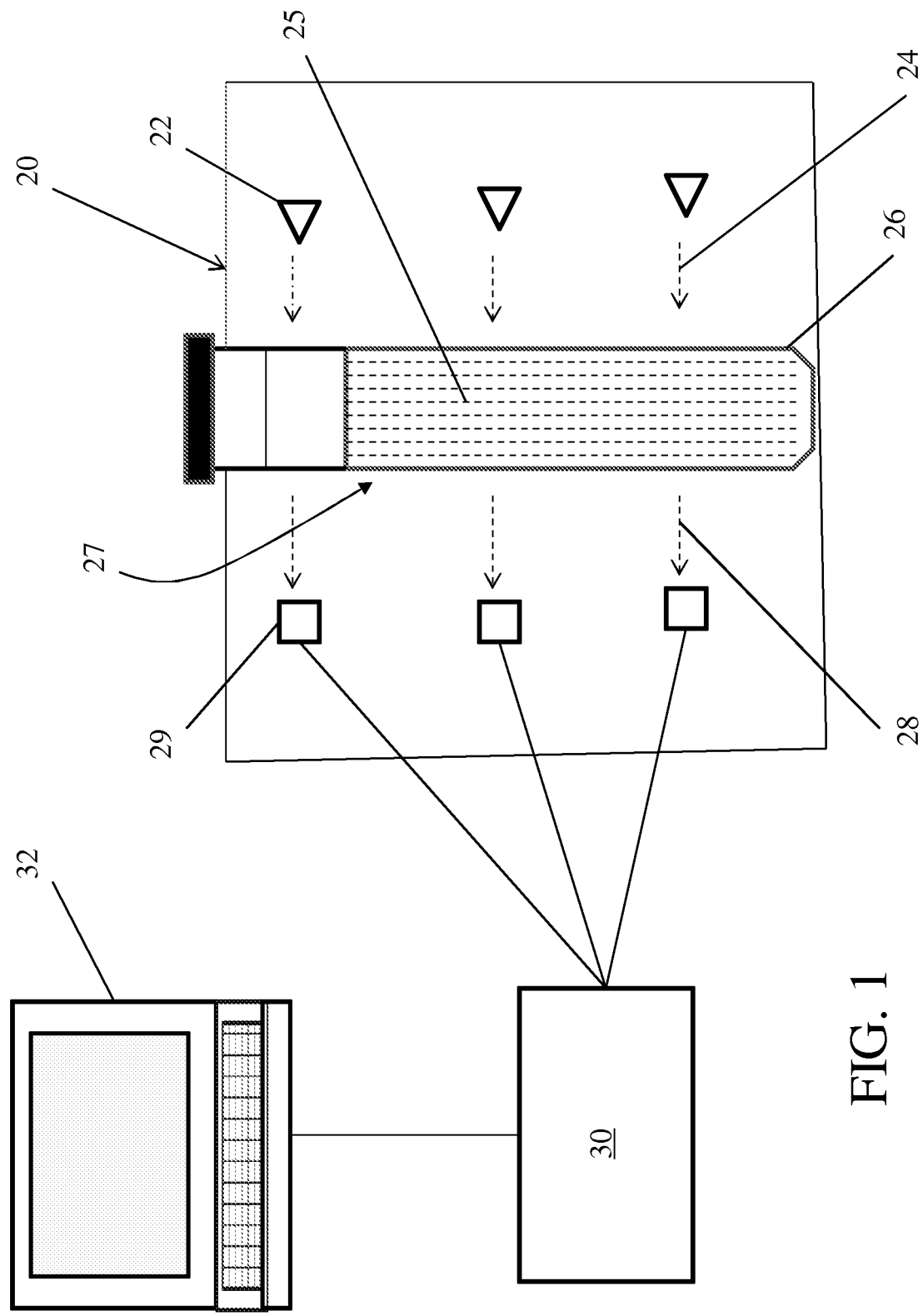
FIG. 1 is a schematic view of the gluten meter.

As shown schematically in FIG. 1, the present apparatus 20 uses a plurality of fixed light sources 22 to pass a light beam 24 through a sedimenting column of hydrated wheat meal or flour 25 in a transparent vertical container 26. Photodetectors 29 juxtaposed opposite the respective light sources 22 measure the response of the light beam 28 as it emerges from the container 26. The light response is recorded in real time on the order of every few milliseconds and the measured response data is directed to a computer processor 30. The processor 30 calculates—in real time—numerical values associated with the properties for the tested sample.

For the purposes of this disclosure, the phrase "in real time" means that the processor 30 can record and calculate protein quality values immediately upon conclusion of the photodiode data collection period. Essentially, there is no significantly time lag between the completion of the sedimentation test and the calculation of numerical values for the properties of the tested substance 25.

In the preferred embodiment, the apparatus 20 measures protein quality and is designated as a "gluten meter". The light sources comprise lasers 22 and the detectors comprise photodiodes 29. Specifically, three lasers 22 and three corresponding photodiodes 29 are positioned near the top, the bottom and mid-height of the column 27. The column of wheat or flour 26 is placed in a glass container and hydrated with sodium dodecylsulfate in lactic acid.

Note that in FIG. 1, reference numbers are only assigned to a single exemplary laser 22, entering 24 and emerging 28 light beams, and photodiode 29. However, three of each element/component 22, 24, 28, 29 are shown in FIG. 1.

In alternative embodiments, there may be more or fewer than three light sources 22. Increasing the number or light sources 22 provides more data and facilitates the generation of more detailed information regarding the properties of the sample 25, however the basic (and most immediately useful) information can be obtained by using the three lasers 22/photodiodes 29 described in the preferred embodiment.

In addition to lasers 22, non-laser light sources should be considered within the scope of the invention. Similarly, alternative types of photodetectors 29 (other than photodiodes) may also be used to measure the beam of light penetrating the sedimenting wheat or flour column 27. Additionally, physical qualities other than protein quality may be derived from the use of the apparatus 20. The container 26 may comprise a cuvette or may have any form known in the art consistent with the function of allowing a light beam to pass through the container 26 so that the emerging light beams 28 can be detected.

Other 'solvents' may be used, either with or without sodium dodecyl sulfate and lactic acid. These solvents may include plain water, or organic solvents such as ethanol-water. The use of tissue or constituent-specific dyes (such as fluorescent dyes) should also be considered within the scope of the invention. Dyes that bind protein or cell wall material and other dyes that affect the penetration of light may yield additional data about the properties of the sample 26. Enzymes or chemical reactants may also be used. In yet another embodiment, lasers of different wavelengths may be used to specifically match fluorescent dyes, etc. Lens (i.e. light wavelength) filters may be positioned in front of diodes to facilitate measurement of specific grain properties and constituents.

Generally, in the preferred embodiment, an operator first calibrates and tests the measurement system to ensure communication between an internal serial analyzer program of the processor 30 and the gluten meter apparatus 20. The operator places ground flour (or other cereal grains) 25 in a vertically oriented glass test tube 26 and hydrates the sample 25 with one-half volume of water, and then adds one-half volume of a sodium dodecyl sulfate and lactic acid solution and mixes the contents. The operator then initiates the test. The exact time required to conduct the test is a function of the characteristics of the tested sample 25, however in the preferred embodiment, salient information is obtained at the conclusion of a photodiode data collection period—which is typically about two to six minutes.

During the test, a plurality of lasers 22 generate respective light beams 24 that passes through the container 26 and the material in the sediment column 27. The emerging light beams 28 impinge on respective photodiodes 29. The photodiode 29 translates the received light beam 28 into an electronic signal and communicates the signal to the processor 30. A monitor 32 attached to the processor 30 may display a graphical representation of the signals received by the process 30 from the photodiodes 29.

Figure 2:
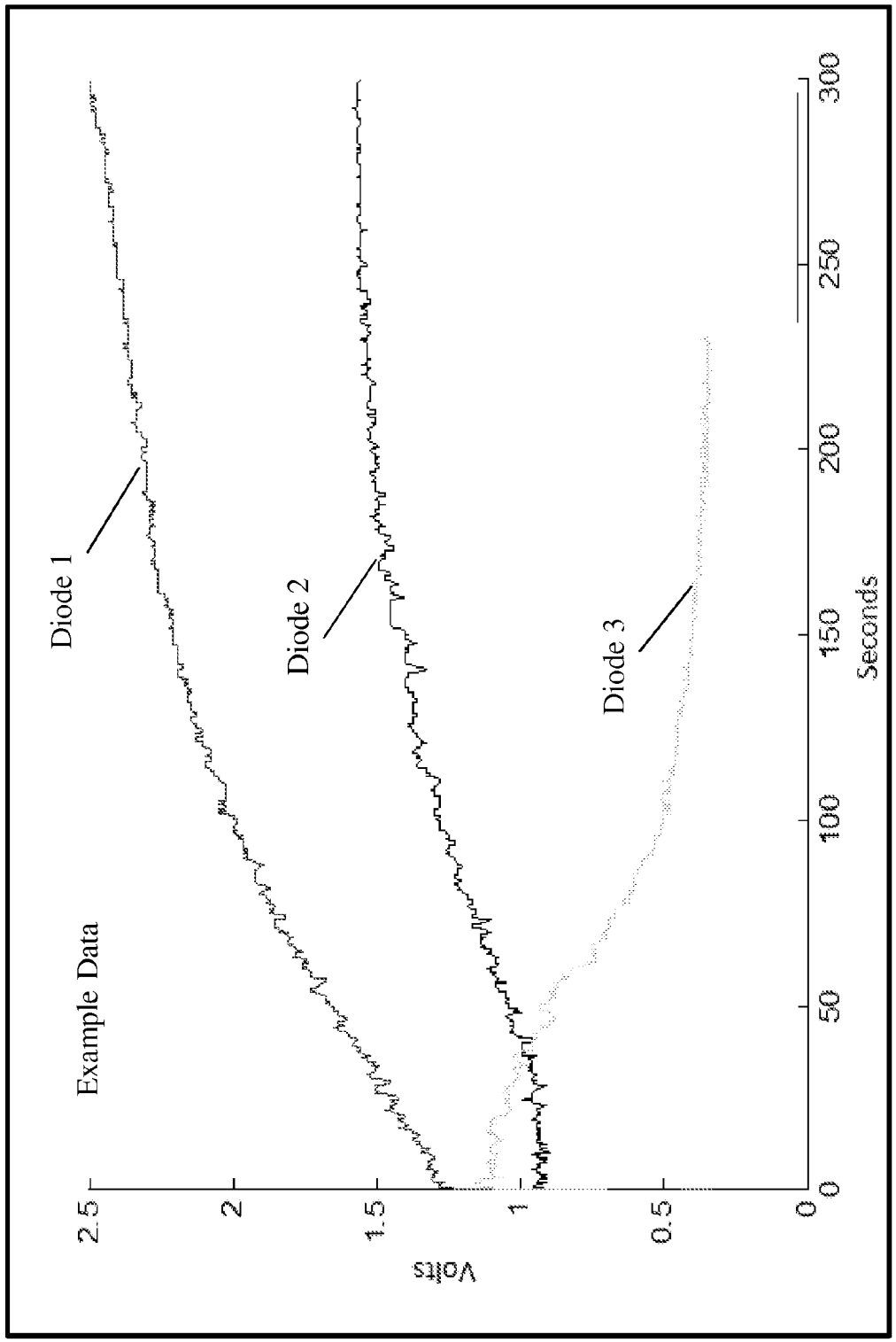
FIG. 2 is a graph showing photodetector (for example photodiode) response in volts as a function of time, as measured by three exemplary photodiodes.
Figure 3:
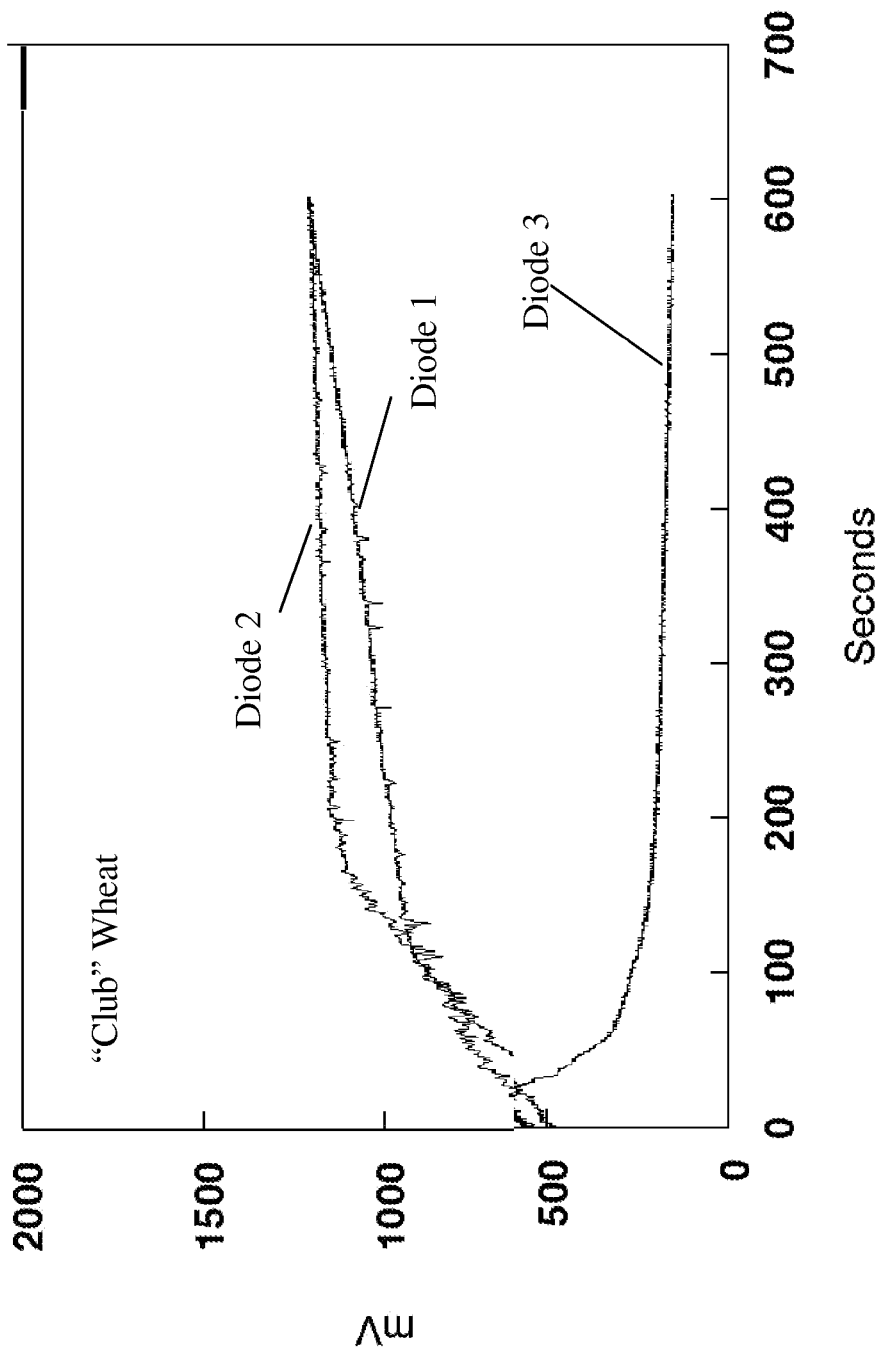
FIG. 3 is a graph showing photodiode responses associated with "Club" wheat. Club wheat typically has very weak gluten.
Figure 4:
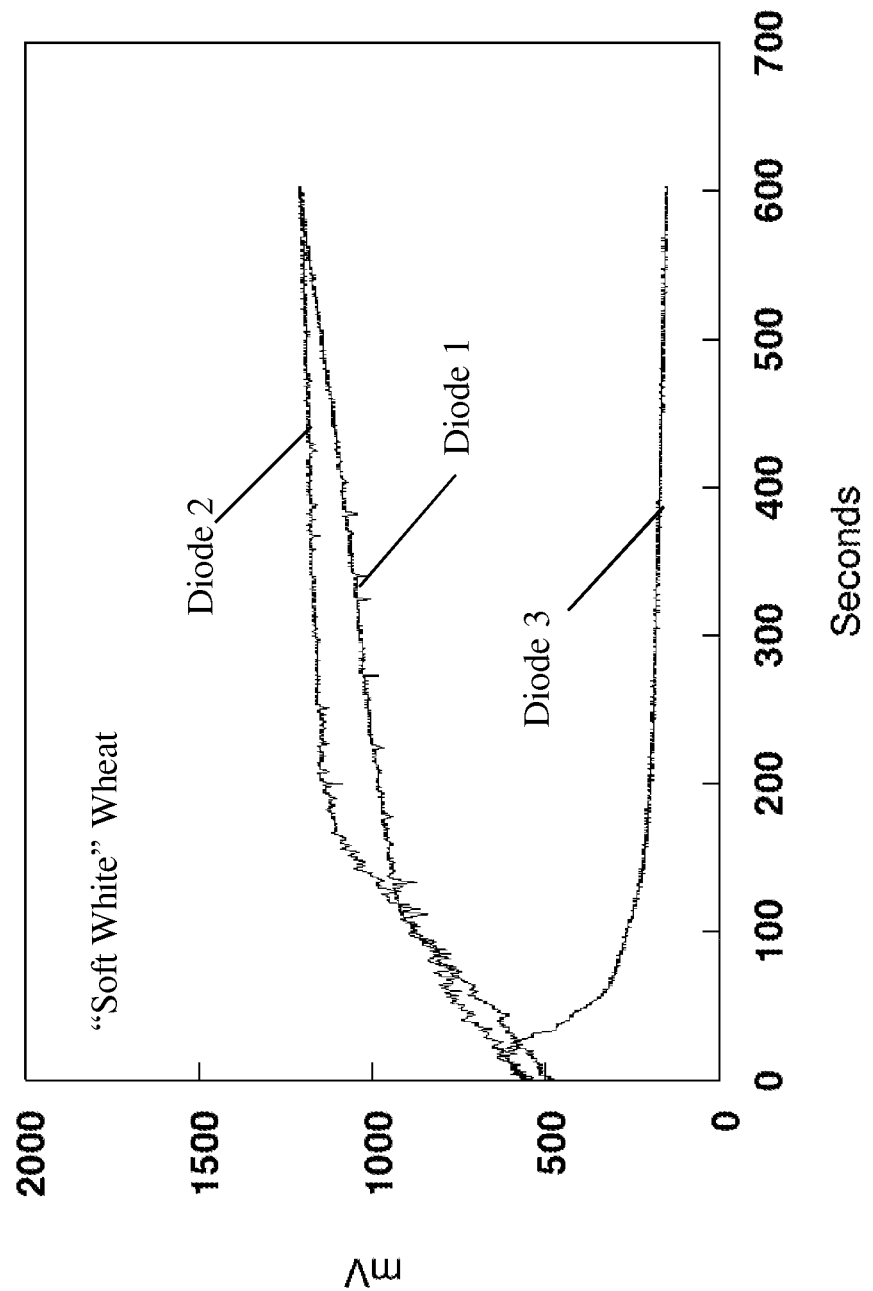
FIG. 4 is a graph showing photodiode responses associated with "Soft White" wheat. Soft White wheat typically has moderately weak gluten.
Figure 5:
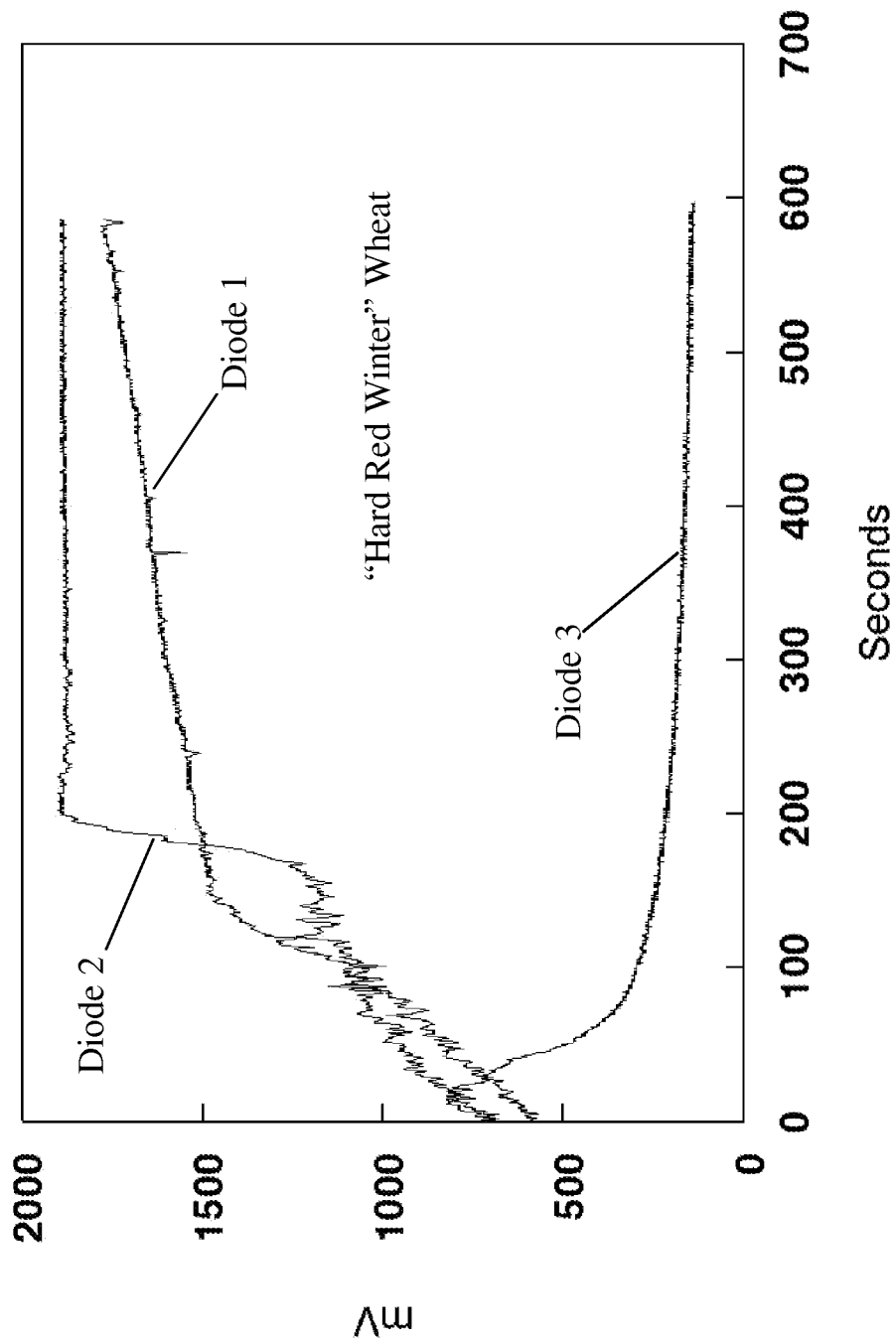
FIG. 5 is a graph showing photodiode responses associated with "Hard Red Winter" wheat. Hard Red Winter wheat typically has moderately strong gluten.

The sedimentation process/test used in the disclosed method translates the time-spatial photodiode 29 response values into measurements expressed as voltage vs. time. An example of the graphical representation of this means of expressing the photodiode 29 data is shown in FIG. 2. The voltage vs. time values expressed in the graph are primarily a function of light absorption-scattering interaction properties of the sample column 27, which are in turn a function of the particle settling rate and therefore indicative of the physical properties of the sample 25 such as the visco-elastic properties of gluten, the molecular weight distribution of the gluten components, (especially the High Molecular Weight glutenin subunits) and the density of the sample 25.

The raw data measured at the photodiodes 29 can be assembled, analyzed, and manipulated in multiple ways to produce information regarding the protein quality and gluten strength of an investigated sample 25. In the preferred embodiment, the photodiode 29 data are processed to generate three photodiode 29 data sets so that one data set is generated for each photodiode 29. Nonlinear regression methods are applied to each data set to generate parameters that characterize the time response of each photodiode 29.

For example, the response of the intermediate photodiode 29 of FIG. 2 can be described as sigmoidal, typified as gradual change soon after the start of the test, followed by a rapid increase in measured light intensity as larger particles pass out of the zone of this detector 29 during settling, and on to an eventual plateau in signal response as the sedimenting column approaches quasi equilibrium. In this case, the sigmoidal function:

$$y = y_0 + \frac{a}{1 + e^{-(\frac{x-x_0}{b})}}$$

is assumed for the response and the regression procedure is used to obtain values for $y_0$, a, b, and $x_0$. This methodology is also applied to the data sets for the first and third diodes 29, and values for $y_0$, a, b, and $x_0$ are also obtained.

These parameters are used in either a linear regression model or a nonparametric structure to predict sedimentation volumes that would have been generated had the conventional sedimentation test run its 30-60 minute course. Some empirical data may be used to fine-tune the mathematically projected sedimentation volumes.

At the end of the process a "Gluten Quality Index" value is assigned to the sample based on the sedimentation volume projected by the mathematical/empirical model. A Gluten Quality Index value is a means of expressing protein quality and gluten strength. Based on the predicted sedimentation results, the sample associated with FIG. 2 data yields a Gluten Quality Index value of (for example) 25.

Alternatively, a Gluten Quality Index value may be assigned directly based on the data profile of the sample 25 as indicated by the three photodiode 29 data sets. Essentially, the data profiles (which may be in the form of coordinates) are electronically compared to a user-generated data base and the Gluten Quality Index value is assigned directly. In one alternative embodiment, the processor 30 searches the data base and assigns a Gluten Quality Index value for the sample 25 based on which previously established (and stored) data base profile the sample 25 most closely resembles. The user-generated data base is empirical and is based directly on the experience of the data base contributors by industry personnel.

For example, the sample 25 data associated with the response may be expressed periodically in the form of x and y coordinates. In one embodiment, "Seconds" are represented as the "x" coordinate, and "Volts" are represented as the "y" coordinate. Using this methodology, a data set for the intermediate photodiode (Diode 2) 29 shown in FIG. 2 would be (50, 1.0), (100, 1.25), (150, 1.45) (200, 1.55), (250, 1.6). Since the "x" coordinate is always in 50 second intervals, a simplified data set could also be expressed in terms of the "y" coordinate as (1.0, 1.25, 1.45, 1.55, 1.60).

Using the same methodology, the FIG. 2 data set for Diode 1 is (1.70, 2.05, 2.25, 2.35, 2.4) and Diode 3 is (0.85, 0.50, 0.40, 0.30, 0.30). An electronic search of the empirical data base indicates that samples with similar data profiles are assigned a Gluten Quality Index value of (for example) 25.

Note that the non-limiting example described above is shown for the purpose of illustrating a simplified method of determining a measure of protein quality. In practice, the measurement interval is likely to be considerably less than 50 seconds and considerably more than five data points are used to determine the Gluten Quality Index value. However, the methodology described above remains applicable even as the size of the data set increases.

Photodiode Data Examples

Figure 6:
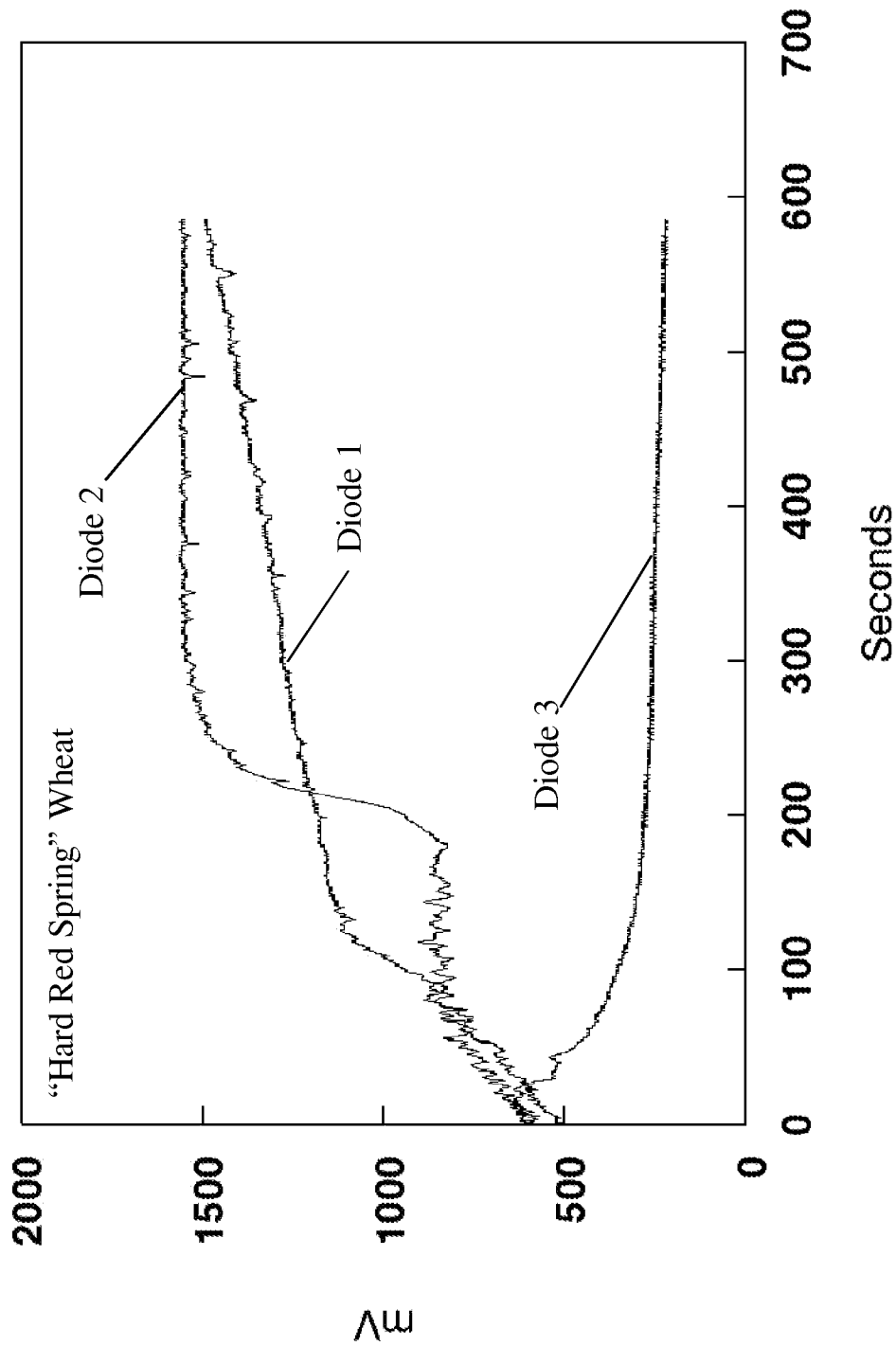
FIG. 6 is a graph showing photodiode responses associated with "Hard Red Spring" wheat. Hard Red Spring wheat typically has very strong gluten.

FIGS. 3-6 show a variety of photodiode data curves that range from a very weak gluten (FIG. 3 "Club" wheat) to very strong gluten (FIG. 6 "Hard Red Spring" wheat).

Methodology Example

A more detailed example of the inventors' protein quality measurement method is described below. Component reference numbers used in the method below are shown in FIG. 1. The method is comprised of the following steps:

1) Prepare a sodium dodecyl sulfate (SDS) liquid mixture by dissolving 20 g of SDS in about 950 mL water. Add 20 mL 1.2 N lactic acid to the mixture. Add additional water to bring the mixture volume to 1 liter and pour the mixture into an automatic pipettor jug.

2) Turn on the computer/processor 30 and the gluten meter 20. Prepare computer/processor 30 to receive data.

3) Grind 250 g of a designated test sample 25 (for example wheat) in a Perten 3100 Falling Number Grinder. Alternatively, an equivalent grinder may also be used. An equivalent grinder would be a "hammer type cyclone mill", whereby the hammer rotates at about 16,800 rpm and forces the ground sample through an approximately 0.8 mm aperture screen to produce a fine, homogeneous sample. Other types of grinders that produce equivalent results may also be used.

4) Add 1.83 g (12% moisture basis) of the ground sample 25 into a glass mixing tube 26.

5) Add 29 mL of water into the mixing tube 26.

6) Agitate the mixing tube contents 27 by running 2 cycles (at 3 seconds per cycle) on Shakematic 1095. Alternatively, the mixing tube contents 27 may be agitated (and thereby mixed) by any means known in the art so long as the ground sample 25 is fully suspended in the SDS, lactic acid, and water solution.

7) Add 29 mL of the SDS-lactic acid solution into the mixing tube 26 (from the automatic pipettor jug)

8) Invert the mixing tube 26 ten times by hand, gently (about 1 sec per inversion) and allow any sediment to re-suspend.

9) Place the mixing tube 26 at about a 30° incline and pause the mixing process for about one minute.

10) Invert the mixing tube 26 ten times by hand, gently (about 1 sec per inversion) and allow any sediment to re-suspend.

11) Place the mixing tube 26 at about a 30° incline and pause the mixing process for about one minute.

12) Invert tube 26 ten times by hand, gently (about 1 sec per inversion), allow any sediment to re-suspend.

13) Insert the mixing tube into the gluten meter 20 and begin collecting data immediately.

14) Collect and process photodiode data as required. The photodiode data collection period is typically 2-6 minutes.

15) Protein quality measurement is produced in real time at the conclusion of the photodiode data collection period Note that in alternative embodiments, steps 8-12 may be automated.

For the foregoing reasons, it is clear that the invention provides an innovative means of determining protein quality in cereal grains. The invention may be modified in multiple ways and applied in various technological applications. For example, although the use of the instrument 20 has primarily been directed to ground wheat meals and flour, the instrument 20 can also be used to determine protein quality in barley, rye, and other grains. Further, although this disclosure is primarily directed to determining protein quality, the apparatus 20, 30 can also be used to determine other properties such as starch and cell wall properties. Sedimentation rate is also related to solution viscosity, soluble starch content, soluble proteins and pentosans so that the current apparatus 20, 30 may be able to determine these properties as well.

The apparatus described herein may be modified and customized as required by a specific operation or application, and the individual components may be modified and defined, as required, to achieve the desired result. Although most of the materials of construction are not described, they may include a variety of compositions consistent with the function of the invention. Such variations are not to be regarded as a departure from the spirit and scope of the invention, and all such modifications as would be obvious to one skilled in the art are intended to be included within the scope of the following claims.

What is claimed is:

1. An apparatus for determining protein quality, the apparatus comprising:
 a container configured to hold a hydrated sample of grain;
 an array of light sources directed at the container;
 an array of photodetectors, each of the photodetectors being opposite of one of the respective light sources; and,
 a processor in communication with the photodetectors;
 whereby the light sources emit a light beam that passes through a sample of hydrated grain and is received by the detectors and communicated to the processor, the processor generating a value for protein quality.

2. The apparatus of claim 1 wherein the values for protein quality are generated in real time.

3. The apparatus of claim 1 wherein the grain is wheat.

4. The apparatus of claim 1 wherein the container is a glass test tube.

5. The apparatus of claim 1 wherein the sample is hydrated with a sodium dodecylsulfate and lactic acid solution.

6. The apparatus of claim 1 wherein the light sources are lasers so that a laser beam is directed at the container.

7. The apparatus of claim 1 wherein the light detector receives the light beam after it emerges from the container and converts the light beam into an electronic signal.

8. The apparatus of claim 7 wherein the electronic signal is directed to the processor.

9. The apparatus of claim 8 wherein the light detector is a photodiode.

10. The apparatus of claim 1 wherein the apparatus is configured to include three light sources and three photodetectors.

11. The apparatus of claim 10 wherein the three light sources and three photodetectors are configured so that a first light source and a first light detector are located adjacent to a top of the container, a second light source and a second light detector are located adjacent a bottom of the container, and a third light source and a third light detector are located between the first and second light sources and the first and second photodetectors.

12. The apparatus of claim 1 wherein the processor utilizes an algorithm to generate values for protein quality.

13. The apparatus of claim 1 further comprising a computer display screen in communication with the processor.

14. The apparatus of claim 13 wherein the computer display graphically displays voltage versus time for each of the photodetectors.

15. A method for determining protein quality, the method comprising:
   (a) providing a container:
   (b) positioning an array of light sources along one side of the container so that the light sources are directed at the container;
   (c) positioning an array of photodetectors on an opposite side of the container from the light sources; and,
   (d) filling the container with a sample of grain;
   (e) hydrating the sample with a hydrating fluid, thereby creating a sedimenting column of hydrated grain;
   (f) directing a light beam from each of the light sources through the sedimenting column to a corresponding photodetector, each of the photodetectors translating the light beam into an electronic signal; and
   (g) generating a value for protein quality.

16. The method of claim 15 wherein in step (g), the photodetector is connected to a computer processor and the computer processor generates a value for protein quality.

17. The method of claim 15 wherein in step (b) the light sources comprise lasers.

18. The method of claim 15 wherein in step (c) the photodetectors comprise photodiodes.

19. The method of claim 15 wherein in step (d) the grain comprises ground wheat.

20. The method of claim 15 wherein in step (e) the hydrating fluid comprises a sodium dodecylsulfate and lactic acid solution.

* * * * *